(12) United States Patent
Melnikov et al.

(10) Patent No.: US 6,658,944 B2
(45) Date of Patent: Dec. 9, 2003

(54) SIMULTANEOUS DETERMINATION OF MULTIPHASE FLOWRATES AND CONCENTRATIONS

(75) Inventors: Vladimir Melnikov, Novgorod (RU); Vladimir Drobkov, Moscow (RU); Andrey Shustov, Moscow (RU)

(73) Assignee: Nest International N.V., Willemstad (AN)

(*) Notice: Subject to any disclaimer, the term of this patent is extended or adjusted under 35 U.S.C. 154(b) by 0 days.

(21) Appl. No.: 10/176,941

(22) Filed: Jun. 21, 2002

(65) Prior Publication Data

US 2003/0051558 A1 Mar. 20, 2003

Related U.S. Application Data

(63) Continuation of application No. PCT/NL01/00180, filed on Mar. 5, 2001.

(30) Foreign Application Priority Data

Mar. 9, 2000 (NL) ............................. PCT/NL00/00159

(51) Int. Cl.⁷ .................................................. G01F 1/74
(52) U.S. Cl. ................................................... 73/861.04
(58) Field of Search ......................... 73/861.04, 861.01, 73/861.02, 61.44, 861.05, 861.08, 861.32

(56) References Cited

U.S. PATENT DOCUMENTS

| | | | | |
|---|---|---|---|---|
| 4,236,406 A | * | 12/1980 | Reed et al. ................ | 73/61.45 |
| 5,049,823 A | * | 9/1991 | Castel et al. ............... | 324/640 |
| 5,287,752 A | | 2/1994 | Den Boer | |
| 5,351,521 A | * | 10/1994 | Cracknell ................... | 73/19.1 |
| 5,367,911 A | | 11/1994 | Jewell et al. | |
| 5,576,495 A | * | 11/1996 | Vetterick .................. | 73/861.04 |
| 6,155,102 A | * | 12/2000 | Toma et al. ............... | 73/61.44 |
| 6,182,505 B1 | * | 2/2001 | Segeral ...................... | 73/61.44 |
| 6,343,516 B1 | * | 2/2002 | Marrelli ................... | 73/861.04 |

FOREIGN PATENT DOCUMENTS

| | | |
|---|---|---|
| DE | 19632529 A1 | 2/1998 |
| EP | 0684458 A2 | 11/1995 |
| RU | 2126143 | 2/1999 |
| RU | 2138023 | 9/1999 |
| WO | WO98/52002 | 11/1998 |

\* cited by examiner

*Primary Examiner*—Edward Lefkowitz
*Assistant Examiner*—Jewel V. Thompson
(74) *Attorney, Agent, or Firm*—Troutman Sanders LLP; Ryan A. Schneider, Esq.

(57) ABSTRACT

The present invention relates to a method and a device for measuring volume flow rates of liquid phase components and gas and determination their volume concentrations in a multiphase mixture along a pipeline. Measurements are executed with an ultrasonic system which includes a set of local acoustic transducers arranged in the interior of the pipeline. Each pair of an emitter and a receiver of the transducer forms a sampling volume of a medium being under control. Volume concentrations of mixture components are determined by timing of passage of acoustic pulses through the sampling volume of the medium. Volume flow rates of the mixture components are calculated by measuring phase velocities and volume concentrations in two pipeline divisions with different cross-section areas located in series at a distance one from the other in flow direction.

24 Claims, 11 Drawing Sheets

US 6,658,944 B2

SIMULTANEOUS DETERMINATION OF MULTIPHASE FLOWRATES AND CONCENTRATIONS

CROSS-REFERENCE TO RELATED APPLICATION

This is a continuation application of PCT/NL11/00180, filed Mar. 5, 2001, which PCT application claims priority of international patent application number PCT/NL00/00159, filed Mar. 9, 2000, both herein incorporated by reference.

FIELD OF THE INVENTION

The invention relates to a method and a device for determination volume flow rates and volume concentrations of liquid phase components and gas in multiphase liquid/gas mixtures such as oil well fluids, composed of oil, water and gas. In particular the invention relates to such a method and such a device according to the preambles of claims 1 and 15 respectively.

BACKGROUND OF THE INVENTION

An effluent flowing along a pipeline from an oil well is a multiphase mixture of oil, water and gas. Accurate and simultaneous measurement of flow rates and volume concentrations of mixture components is important for control of the well operation.

Methods and devices for measuring these flow characteristics accepted up to the present demand preliminary separation of gas in special separators which are installed in measuring devices on the territory of oil fields. This fact leads to considerable capital expenses by execution of such measurements.

Techniques for measuring of the said multiphase flow characteristics without a prior separation of gas phase are also known. These methods and devices are based on various physical principles: difference of density and electromagnetic characteristics of the components, interaction with gamma-rays and ultrasonic waves, and others.

RU-C-2138023 discloses a method and device according to the preamble of claim 1 and to the preamble of claim 15 respectively. With the prior art method at one location along a pipeline, which passes a multiphase mixture with constant flow velocity, the acoustic conductivity of the mixture is measured by transmitting acoustic pulses through a controlled volume of the mixture by a transmitter and counting these pulses if received by a receiver, and with a ratio of transmitted and received pulses representing the amount of a phase of the mixture. In addition, at each of two locations the time it takes for a pulse to transit through a controlled volume is measured, said time is cross correlated with that obtained from the other location and then used in combination with a value of the distance between said locations to calculate the velocity. During equipment calibration using clean oil and clean water, times of impulse transit through a controlled volume is measured and used in combination with an actual (in situ) measured transit time, said phase amount ratio, said velocity and a value of the cross section of the pipeline to calculate the actual flow rates of gas, oil and water.

EP-A-0684458 discloses a multiphase flow meter in which a pipeline comprises two restrictions, which each provide a change of velocity of the flow with respect to the flow velocity in locations just before and in each restriction respectively. For each restriction a pressure difference between said locations is measured. A value for the volume V between the restrictions must be determined in advance. By using pressure difference signals and the volume value V the total volume flow rate q can be determined. By measuring a static pressure difference a first approximation of the density p of the mixture can be determined. A further device is used to provide one or more indications about the composition of the multiphase mixture. Given the densities $\rho_o$, $\rho_w$, $\rho_g$ of the components of the multiphase mixture, the flow rates of the phases are determined. With this prior art flow meter, at locations where the velocity of the mixture has been changed, that is at each restriction, the velocity is not measured itself. Neither is the velocity measured at a distance from the restriction. Instead, a pressure difference at each restriction must be measured to therefrom determine a time wich the mixture takes to travel from the one restriction to the other restriction. From said time and the known distance between the restrictions the velocity is calculated.

U.S. Pat. No. 5,287,752 describes a device for determination flow rates of multiphase fluids by means of a set of capacitors placed on two parallel plates which are arranged inside a horizontal or inclined pipeline parallel to a flow direction. In order to determine a water/oil volume proportion and a part of pipeline cross-section occupied by liquid phase impedances of a medium located at the moment in measuring cells of all elementary capacitors are measured. A velocity of the liquid phase is determined by measuring and cross-correlation impedances of elementary capacitors located in a matrix row situated in a part of cross-section occupied by the liquid phase. A velocity of gas is determined by measuring passage time of structural deformations of the flow in the upper part of the pipeline. Volume flow rates of the phases are determined taking into account the parts of the pipeline cross-section occupied by the liquid and gas phases of the flow.

The proposed method has limited sphere of application since it can be effectively used only by an intermittent flow regime. Besides a type of emulsion and dispersion of components aren't taken into account in this method.

U.S. Pat. No. 5,367,911 describes an apparatus for sensing fluid behaviour in a conduit that can be used as a flow meter. The measuring device includes at least two sensors arranged within a pipeline, one downstream the other. The sensors may include acoustic transducers or electrical conductivity (or resistivity) sensors. Each sensor provides an output data signal, indicative of the measured physical property of a medium flowing in respective sampling volumes. Output signals are processed in a circuit and are cross-correlated. Since a distance between the sensors is known a calculation of the flow speed is made.

However the authors of the patent don't take into account that a gas phase moves relative to a liquid phase in multiphase flows.

European patent A 0684458 relates to a method and a device for measuring flow rate of multiphase fluids. The device comprises two sections situated at a distance one from the other along a duct. The sections are implemented in the form of venturis. Each section includes a passage with different cross-section areas provided with means for inducing a change of speed therein and a variation of dynamic pressure correspondingly. Besides the device includes appropriate means for measuring the resulting pressure differences. Two pressure difference signals obtained in the said respective sections are suitable for cross-correlation to produce a third signal representative of a total volume flow rate. In order to determine the flow rates of phases another pressure difference is measured in a venturi type flow section and the signal that is a function of the total mass flow rate Q and density ρ of a mixture is obtained. One more pressure difference is measured in the section of a "gradiomanometer" type. This section is disposed in a portion of a vertical duct that has constant cross-section area. In a conventional manner the latter pressure difference represents a static pressure difference that is proportional, to a first approximation, to the density p of the mixture. In addition, the device includes a module situated in the duct, that provides one or more indications of composition of the multiphase fluid, in other words, determines volume or mass concentrations of components constituting the fluid. A processor calculates the mass flow rate Q via parallel paths depending on gas content. When the gas content is moderate (<65%) a first processing way is used on the basis of a signal proportional to the expression $Q^2/\rho$ and a signal representative of the density ρ of the mixture. A second processing way based on a signal representative of the total volume flow rate and a signal representative of the density p of the mixture is used when the gas content is high (>65%).

It is necessary to note that devices with venturi type sections have a small dynamic range and hence may be used in a limited range of flow rate measurements. Besides, a flow rate factor of such devices significantly depends on gas content that influences on the measurement accuracy. In the described device the gas content is calculated but not measured that also decreases the measurement accuracy. Using the device for measuring the flow rate of oilwell effluents containing crude oil may lead to clogging of its pressure takeoffs.

SUMMARY OF THE INVENTION

The present invention provides a method and a device for determination volume flow rates of multiphase mixture components along a portion of a pipeline without prior separation of gas.

The present invention provides measuring volume concentrations of the multiphase mixture components along the portion of the pipeline.

The invention also provides a method and a device for measuring the above-mentioned characteristics of a multiphase medium with different types of flow.

The invention ensures obtaining reliable data of measuring characteristics of effluents with different sizes of gas inclusions.

Besides the invention secures compactness of the device and its simple portability.

The above-mentioned features are achieved through the method for determination volume flow rates of liquid components and gas in the multiphase mixture flowing along a pipeline according to which a measuring flow cell installed into a pipeline includes two pipeline sections, called divisions in the description also, located in series in the flow direction and having different flow section areas: $F_2=k F_1$ (diameter $D_2=D_1\sqrt{k}$) $k \neq 1$.

When k≈0.5 changing of the flow section area induces significant changing of a liquid phase velocity and correspondingly of a real gas phase velocity in the measuring pipeline divisions ($\overline{w}_{g,1} < \overline{w}_{g,2}$) while changing of a relative velocity of gas inclusions and of a real volume gas concentration $\overline{\phi}$ in the mixture is insignificant. Calculation analysis of a mixture flow model has allowed to derive a formula for determination a liquid phase volume flow rate for the multiphase flow passing through the calibrated pipeline divisions:

$$Q_l = k/(1-k) F_1 [\overline{w}_{g,2}(1-\overline{\phi}_2) - \overline{w}_{g,1}(1-\overline{\phi}_1)].$$

A gas volume flow rate is determined by the following formula:

$$Q_g = F_1 \overline{w}_{g,1} \cdot \overline{\phi}_1 = F_2 \overline{w}_{g,2} \cdot \overline{\phi}_2.$$

The real velocities of gas phase $w_g$, the volume concentrations of gas $\overline{\phi}$, the volume concentrations of liquid components, such as water W and oil (1−W) in the calibrated pipeline divisions are determined by means of ultrasonic sensing sampling volumes of the multiphase flow with a set of transducers arranged within the measuring pipeline divisions along a radius of a flow section. These transducers serve as emitters and receivers of acoustic signals in sampling volumes.

Obtained values of local characteristics of the multiphase flow are then averaged over cross-section areas of the measuring pipeline divisions.

Measuring of the real gas velocity is executed by cross-correlation of sensor signals or by Doppler's method.

Measuring of the volume concentration of gas is executed through indication of acoustic conductivity of the sampling volumes of the medium.

Ultrasonic measuring of the volume concentration of liquid phase components is based on determination of time of acoustic pulses pass through the sampling volume since it was found that in a fluid such as water/oil mixture the time of signal pass depends practically linearly on a proportion of the volume concentrations of these components regardless emulsion type.

The mentioned features are also provided by the apparatus for determination volume flow rates and volume concentrations of liquid components and gas of a liquid-gas multiphase mixture flowing along a pipeline including a measuring flow cell being installed in a pipeline. The measuring flow cell comprises two pipeline divisions disposed in series in a flow direction and having different flow section areas: $F_2=kF_1$ (diameter $D_2=D_1\sqrt{k}$)k $\neq 1$.

Changing of a flow section area (when k≈0.5) induces significant changing of a liquid phase velocity and a real gas velocity in the measuring pipeline divisions ($\overline{w}_{g,1} < \overline{w}_{g,2}$) while changing of a relative velocity of gas inclusions and of a real volume gas concentration $\overline{\phi}$ in a mixture is insignificant. A volume flow rate of a liquid phase is determined by a difference of products of the real gas phase velocity $w_g$ by a part of a pipeline section occupied by a liquid phase (1−$\overline{\phi}$) in the first and the second measuring pipeline divisions:

$$Q_l = (k/1-k) F_1 [\overline{w}_{g,2}(1-\overline{\phi}_2) - \overline{w}_{g,1}(1-\overline{\phi}_1)].$$

Gas volume flow rate is determined by the following formula:

$$Q_g = F_1 \overline{w}_{g,1} \cdot \overline{\phi}_1 = F_2 \overline{w}_{g,2} \cdot \overline{\phi}_2.$$

The real velocities of gas phase $\overline{w}_g$, the volume concentrations of gas $\overline{\phi}$, the volume concentrations of liquid components, such as water W and oil (1−W) in the calibrated pipeline divisions of the pipeline are determined by means of ultrasonic sensing local volumes of the multiphase flow with a set of transducers arranged within the measuring pipeline divisions along a radius of a flow section.

The principle of operation of a local gas velocity meter is based on determination a cross-correlation function of an amplitude of a signal of an acoustic conductivity transducer. The two transducers are placed at a fixed distance one upstream the other in the flow direction. The acoustic transducer consists of an emitter and a receiver of ultrasonic pulses providing acoustic illumination of the sampling volume. The transducer may be used as an emitter and a receiver of reflected signals in the "emission-reception" mode.

An electro-acoustic channel of the meter operates in the following way: voltage pulses from a pulse generator come to the emitter where they are converted into ultrasonic pulses. After passing through the sampling volume they are received by the receiver, converted into the voltage pulses, amplified and are sent to a peak detector input which is controlled by strobe pulses. The strobe pulses determine a time interval during which a signal reception is expected. A voltage at the input of the peak detector is proportional to an amplitude of a received signal and is determined by acoustic energy losses in a sensor sampling volume. Output signals of peak detectors come to a calculator which determines a cross-correlation or an autocorrelation function (in case of one transducer) and calculates the real local velocity of gas phase or liquid phase without gas.

Besides the expounded principle Doppler's method for measuring the gas phase local velocity through sensing a medium by ultrasonic pulses directed upstream the flow may be used. In this variant emitter and receivers are also disposed inside the measuring pipeline divisions.

The principle of operation of a volume gas concentration meter is based on indication of acoustic conductivity of a sampling volume. A signal from a voltage pulse generator is sent to an emitter consisting of a transmitter and a waveguide. After conversion acoustic pulses reach the sampling volume through the waveguide, pass through the volume and through a receiving waveguide come to the transmitter where they are transformed into a voltage signal that after amplification comes to a peak detector. A strobe pulse former opens the peak detector for a time while the signal coming is expected. From the peak detector an output signal proportional to an amplitude of the received signal comes to a comparator which compares the output signal of the peak detector with a discrimination level set by a former of discrimination level. An output signal of the comparator comes to a calculator which determines the volume gas content in a medium as a ratio of time of gas phase presence in the sampling volume to the full time of the measurement.

The principle of operation of ultrasonic meter of volume concentrations of liquid components is based on determination time of passage of ultrasonic pulses through a sampling volume of a multiphase flow since it was found that in liquid phase, such as water/oil mixture the time of passage of ultrasonic signal practically linearly depends on relationship of volume concentrations of liquid components regardless emulsion type. A distance between emitter and receiver is chosen so that penetration of large gas inclusions with sizes more than 1 mm is prevented. Voltage pulses from a generator are sent to the ultrasonic emitter which forms acoustic pulses. The acoustic pulses pass through a sampling volume, are received by the receiver and are transformed into a voltage signal which is amplified and then sent to a comparator being strobed. The comparator opens for the time while the reception of the signal is being expected by means of the strobe pulse former that ensures high interference immunity of the scheme. Simultaneously with forming the emitting pulses a scheme forming a pulse duration is activated. This scheme is stopped by the signal coming from the comparator output. So the duration of the output signal is equal to the time of the ultrasonic signal pass from the emitter to the receiver. Then the pulse is transformed into an amplitude signal and comes into calculator which determines volume concentration of liquid phase components.

A processor functioning according to set programs controls operation of the meters of local flow parameters $w_{g,1}$, $w_{g,2}$, $\phi_1$, $\phi_2$, W, averages these parameters over the cross-sections of measuring pipeline divisions and calculates volume flow rates of liquid phase components and gas.

DESCRIPTION OF PREFERRED EMBODIMENT

Figure 1A:
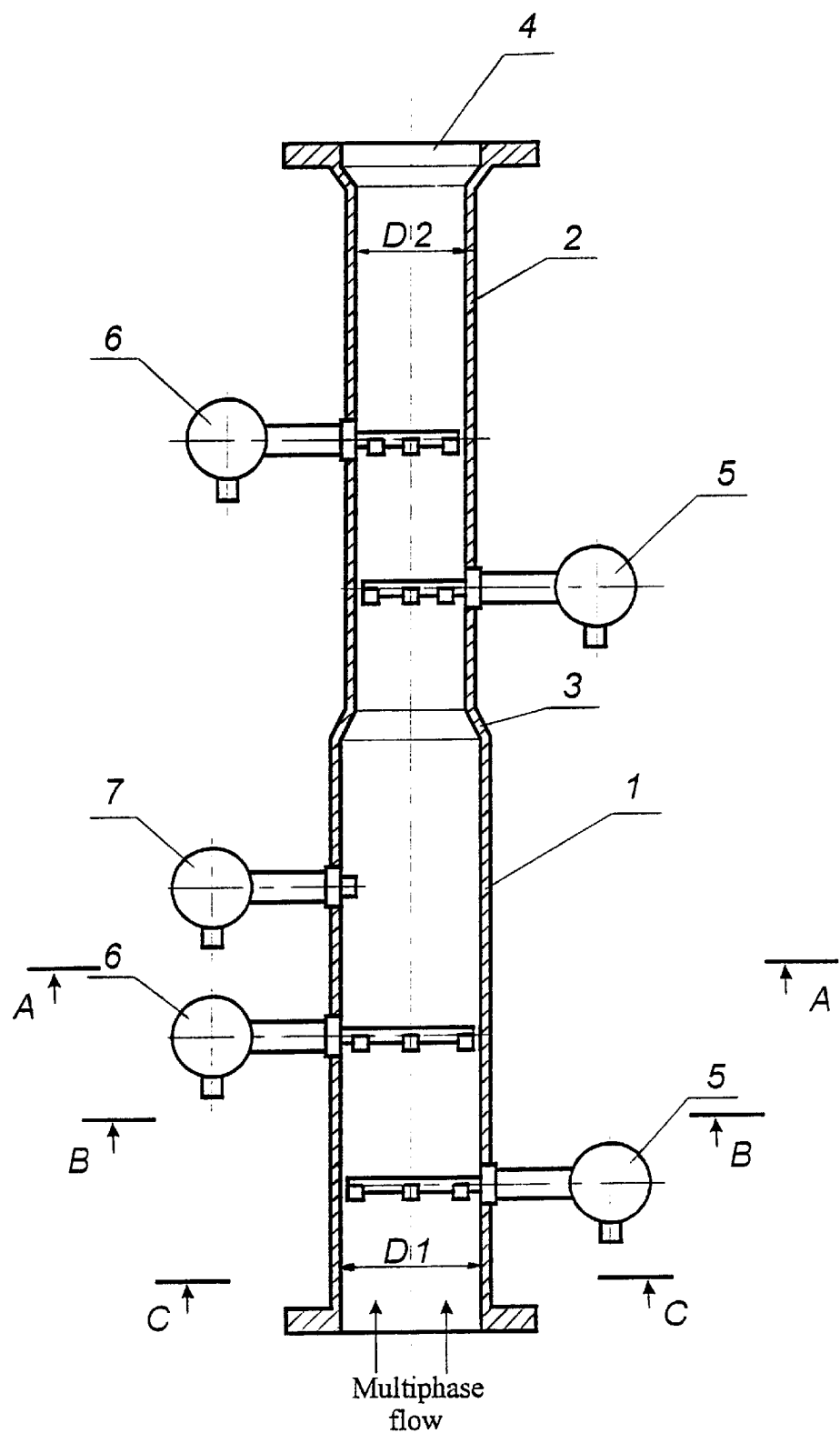
FIGS. 1a, 1b configuration of the multiphase flow rate device proposed within the framework of the present invention.
Figure 1B:
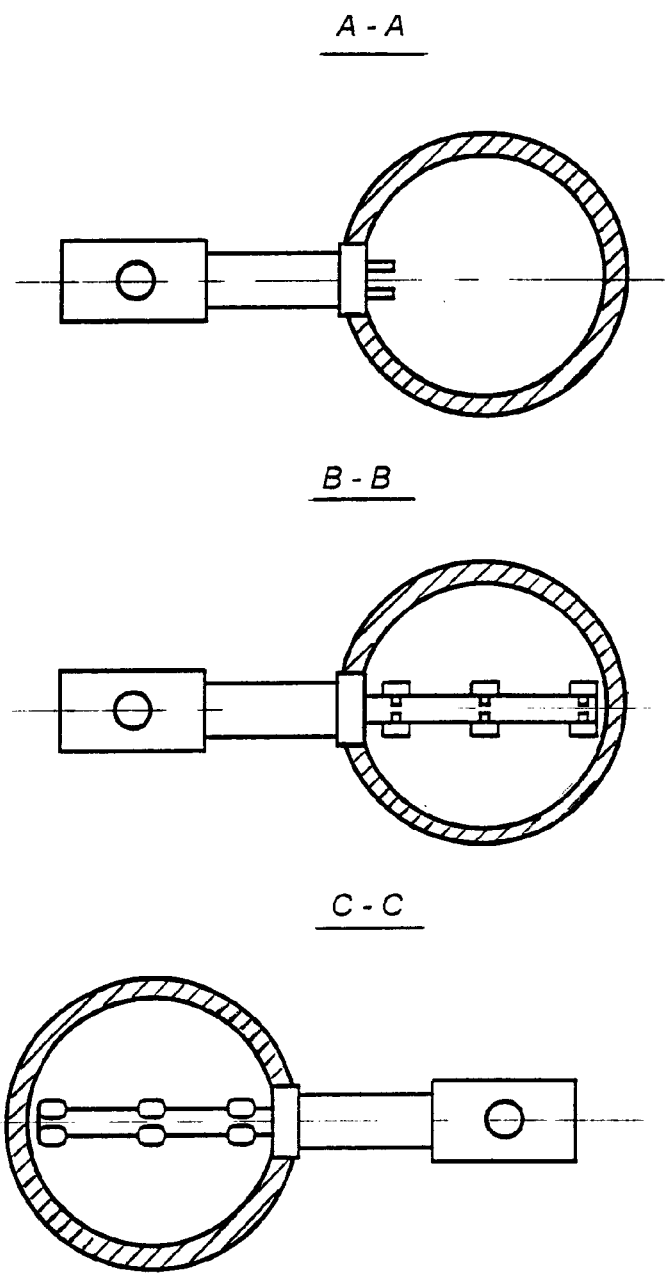

Configuration of a measuring flow cell of the apparatus for determination volume flow rates of liquid components and gas in a multiphase mixture is represented in FIG. 1a and FIG. 1b.

The measuring flow cell is installed into a pipeline by means of flange connections. The flow cell comprises two measuring pipeline divisions 1 and 2 disposed in series in a flow direction and having different flow section areas: $F_2=kF_1$ (diameter $D_2=D_1\sqrt{k}$). For FIG. 1 k<1 holds.

Changing of a flow section area induces significant changing of a liquid phase velocity and a real gas phase velocity in the measuring pipeline divisions with the cross-section areas $F_1$ and $F_2$. In order to ensure minimum hydrodynamic disturbance of the flow a transition from a first division to a second division and back to the initial cross-section area $F_1$ of the pipeline is realized through transition pipeline divisions 3 and 4. Each sensor 5 and 6 of a real velocity meter and a gas content meter includes a set of transducers placed inside the measuring pipeline divisions along radii of the sections. A sensor 7 of the volume concentration meter of liquid components comprises a set of transducers located in a cavity of the first pipeline divisions. To accelerate the process of viscous medium change within the transducer's volumes and for removal of paraffin deposits the sensors are equipped with mechanical cleaning arrangements or electric heaters. The sensors are installed in such a way that they can be removed from the measuring pipeline divisions, for example, for execution of technical maintenance or substitution.

Let us consider separately the meters of multiphase flow parameters being a part of the device and a calculation model of the multiphase mixture flow used for determination of volume flow rates of mixture components.

A calculation model of a liquid/gas mixture where gas inclusions of various size represent gas phase is used to determine flow rates of phases. Averaged physical values are used in formulas.

The real volume concentration of the gas in the i-th cross-section of a flow is:

$$\phi_i = F_{g,i}/F_i, \quad (1)$$

where $F_i = \pi/4\ D_i^2$ is a cross-section area of the i-th pipeline divisions, $F_{g,i}=\phi_i \cdot F_i$ is a cross-section area occupied by gas.

Since $F_i=F_{g,i}+F_{l,i}$, where $F_{l,i}$ is a cross-sectional area occupied by liquid, we can write instead of formula (1):

$$\varphi_i = \frac{w^r_{g,i}}{w^r_{g,i} + w^r_{l,i} \cdot w_{g,i}/w_{l,i}}, \quad (2)$$

where $w^r_{g,i}=Q_{g,i}/F_i$ is a reduced velocity of the gas phase in the i-th pipeline divisions, where $Q_{g,i}$ is a volume flow rate of the gas phase in the i-th pipeline divisions;

$w^r_{l,i}=Q_{l,i}/F_i$ is a reduced velocity of the liquid phase in the i-th pipeline divisions, where $Q_{l,i}$ is a volume flow rate of the liquid phase in the i-th pipeline divisions;

$w_{g,i}=Q_{g,i}/F_{g,i}$ is a real velocity of the gas phase in the i-th pipeline divisions, where $Q_{g,i}$ is a volume flow rate of the gas phase in the i-th pipeline divisions;

$w_{l,i}=Q_{l,i}/F_{l,i}$ is a real velocity of the liquid phase in the i-th pipeline divisions, where $Q_{l,i}$ is a volume flow rate of the liquid phase in the i-th pipeline divisions;

and $F_{l,i}=(1-\phi_i)F_i$ is a section area of the i-th pipeline divisions occupied by liquid.

Since besides $w_{l,i}=w^r_{l,i}/(1-\phi_i)$, and $w_{g,i}=w_{l,i}+w_{g,i}^{rel}$, where $w_{g,i}^{rel}$ is a relative velocity of the gas phase in the i-th pipeline divisions, so we have:

$$\varphi_i = \frac{w^r_{g,i}}{w^r_{g,i} + w^r_{l,i} + (1-\varphi_i)w^{rel}_{g,i}}. \quad (3)$$

According to experimental data relative velocity of the flow of gas bubbles $w_{g,1}^{rel}$ (group velocity of floating-up) is connected with the real volume concentration $\phi_i$ by the following relationship:

$$w_{g,i}^{rel}=w_{g,\infty}/(1-\phi_1), \quad (4)$$

where $w_{g,\infty}$ is average velocity of the individual bubble floating-up in the infinite liquid medium.

Real velocities $w_{g,1}$ and $w_{g,2}$ in measuring pipeline divisions are connected with relative velocities in the following way:

$$w_{g,1}=w_{l,1}+w_{g,1}^{rel} \text{ and } w_{g,2}=w_{l,2}+w_{g,2}^{rel}. \quad (5)$$

Subtracting the first equality (5) from the second one (5) we get the following equality:

$$w_{g,2}-w_{g,1}=\Delta w_g=(w_{l,2}-w_{l,1})+(w_{g,2}^{rel}-w_{g,1}^{rel}), \quad (6)$$

which can be written in the form:

$$\Delta w_g=w^r_{l,2}/(1-\phi_2)-w^r_{l,1}/(1-\phi_1)+w_{g,\infty}[1/(1-\phi_2)-1/(1-\phi_1)] \quad (7)$$

Supposing that we have the following relationships $F_2=kF_1$, where $k\neq 1$, and taking into account that $w^r_{l,i}=Q_{l,i}/F_i$ we get:

$$\Delta w_g = \frac{Q_l}{F_1(1-\varphi_1)}\left[\frac{1-\varphi_1}{k(1-\varphi_2)}-1\right] + \frac{w_{g,\infty}}{1-\varphi_1}\left[\frac{1-\varphi_1}{1-\varphi_2}-1\right] \quad (8)$$

since $Q_{l,i}=Q_l$.

It follows from the relationships (3) and (4) that $$\phi_i=w^r_{g,i}/(w^r_{g,i}+w^r_{l,i}+w_{g,\infty}). \quad (9)$$

After execution of appropriate transformations and taking into account that $Q_{g,i}=Q_g$ we get:

$$1/\phi_i=1+Q_l/Q_g+F_i w_{g,\infty}/Q_g. \quad (10)$$

Substituting the value $Q_g=F_1\phi_1 w_{g,i}$, where $w_{g,i}$ and $\phi_1$—are values being measured we obtain:

$$\frac{1}{\phi_i} = 1 + \frac{1}{\phi_i}\left(\frac{Q_l}{F_i w_{g,i}} + \frac{w_{g,\infty}}{w_{g,i}}\right), \quad (11)$$

$$\text{where from } \phi_i = 1 - \frac{Q_l}{F_i w_{g,i}} - \frac{w_{g,\infty}}{w_{g,i}}. \quad (12)$$

Consequently $Q_l=F_i[w_{g,i}(1-\phi_i)-w_{g,\infty}]$. (13)

It should be noted that in the case of stationary liquid ($Q_l=0$) it follows from the formula (13) the following relationship: $w_{g,i}=w_{g,\infty}/(1-\phi_i)$, what coincides with definition of the relative velocity (4) so that in this case $w_{g,i}=w_{g,i}^{rel}$. It follows from the formula (13) that $$Q_l=F_1[w_{g,1}(1-\phi_1)-w_{g,\infty}] \quad (14)$$

and $$Q_l=F_2[w_{g,2}(1-\phi_2)-w_{g,\infty}]. \quad (15)$$

Having equated relationships (14) and (15) and taking into account that $F_2=kF_1$, where $k\neq1$, we get:

$$Q_l=F_1[w_{g,2}(1-\phi_2)-w_{g,1}(1-\phi_1)]k/(1-k). \quad (16)$$

So the volume flow rate of liquid phase in the calibrated pipeline divisions is determined according to the relationship (16) from the measured real velocities and volume concentrations of gas phase in the first and the second measuring pipeline divisions. If $F_2=0.5F_1$ the expression (16) becomes:

$$Q_l=F_1[w_{g,2}(1-\phi_2)-w_{g,1}(1-\phi_1)]. \quad (17)$$

Besides it should be noted that if $\phi_1=\phi_2=0$ velocity meters shall fix acoustic inhomogeneity of liquid phase and correspondingly velocities $w_{l,1}$ and $w_{l,2}$. So the relationship (16) transforms into the formula $Q_l=F_1\cdot w_{l,1}$, and if $\phi_1=\phi_2=1$ this relationship takes the form $Q_l=0$.

Volume flow rates of liquid phase components are determined by the formulas:

$$Q_{oil}=Q_l(1-W) \text{ and } Q_w=Q_l W, \quad (18)$$

where W is the volume concentration of water in the emulsion.

Volume flow rate of the gas phase is determined by the following relationship:

$$Q_g=\bar{w}_{g,1}\cdot F_1\cdot\bar\phi_1=\bar{w}_{g,2}\cdot F_2\cdot\bar\phi_2. \quad (19)$$

Figure 2:
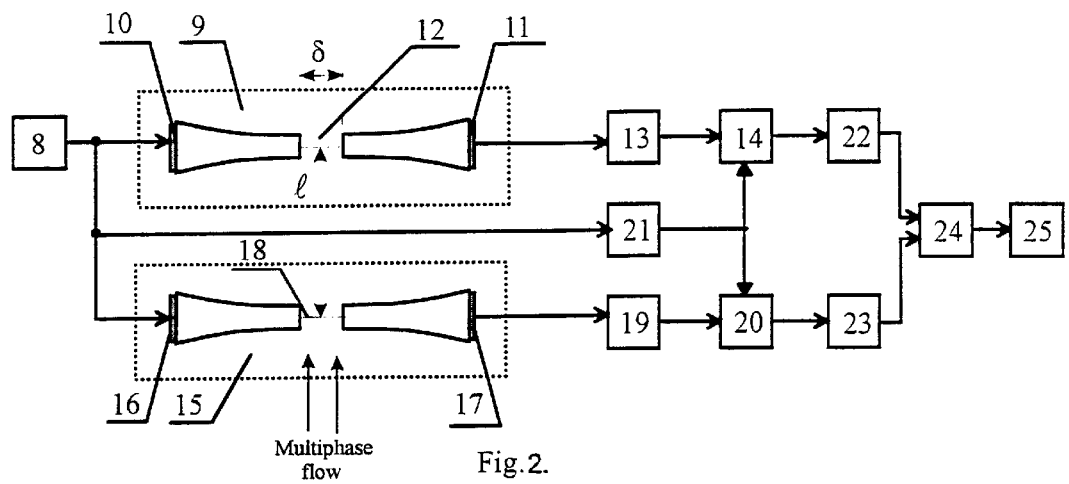
FIG. 2 block diagram of the gas phase local velocity meter for the variant of sequential location of transducers.

FIG. 2 shows a block diagram of an ultrasonic meter of local gas velocity $w_g$ of a multiphase mixture. A circuit of the meter includes: a generator of voltage pulses 8, a first transducer 9 connected in series with the generator 8 and comprising an emitter 10 and a receiver 11 (a gap between them forms a first sampling volume 12), a first amplifier 13 and a first peak detector 14 being strobed. The following elements are connected in series to the generator 8: a second transducer 15 comprising an emitter 16 and a receiver 17 (a gap between them forms the second sampling volume 18), the second amplifier 19 and also the second peak detector 20 being strobed. Besides, former 21 of delayed strobe pulses and the first and the second peak detectors 14 and 20 are connected to generator 8. The latter peak detectors are connected to a calculator 24 and a display 25 respectively through a first and a second analogue-to-digital converter (ADC) 22 and 23.

Sensors 9 and 15 are placed inside the pipeline in such a way that a flow at first passes through the one sampling volume, for example, volume 18, and then through the other, for example, volume 12. The sizes of transducers are chosen in such a way that they induce minimum disturbances of a flow (diameter of transducers $\leq3$ mm). Distance $\delta$ between emitter and receiver makes up about 2 mm and distance l between the lower and the upper pairs of transducers is equal to 3÷5 mm. Waveguides of the first and the second pairs of transducers in plan view of the sensor are located perpendicularly to one another that also improves hydrodynamics of a flow.

Figure 3:
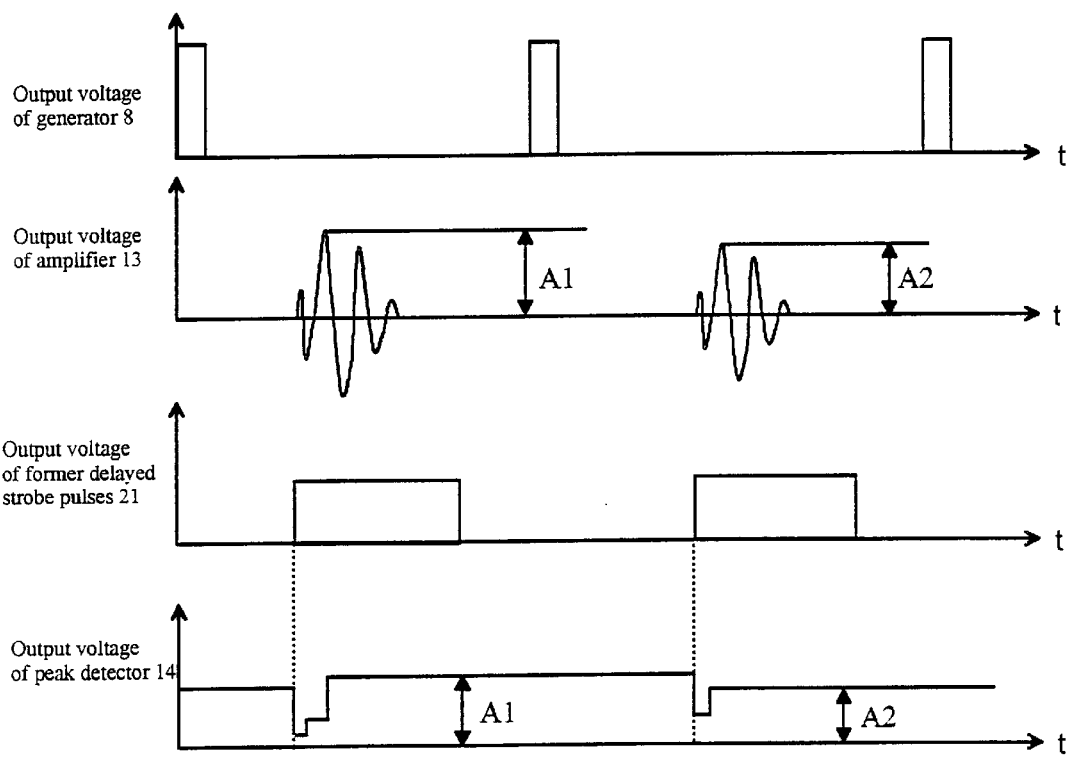
FIG. 3 voltage diagram of the signal processed in the block diagram presented in FIG. 2.

An ultrasonic local velocity meter operates in the following way. Voltage pulses from the generator 8 are transmitted to the emitters 3 and 9, transformed into ultrasonic pulses and pass through the sampling volumes 12 and 18, then they are received by the receivers 11 and 17, transformed into a voltage signal, amplified by the amplifiers 13 and 19 and transmitted to the peak detectors 14 and 20 being strobed. Simultaneously with transmitting of the ultrasonic pulses the passage time of which is determined by a distance between the emitter and the receiver by the fixed pulse frequency the strobe pulses come to strobe inputs of the peak detectors 14 and 20. The strobe pulses switches the peak detectors into an active state. As a result voltage levels proportional to amplitudes of the received acoustic signals are formed at outputs of the peak detectors (see the voltage diagram shown in FIG. 3). After analogue-to-digital conversion in the ADC 22 and the ADC 23 the voltage signals are transmitted to the calculator 24 that calculates a cross-correlation function (CCF) for the received acoustic signals and presents it on the display 25.

Because of discrete structure the multiphase mixture is an acoustically inhomogeneous medium. Hence an amplitude of received signals will fluctuate. Acoustic diffusers (the major part of them are gas inclusions, making the main contribution to diffusion of ultrasonic pulses) induce fluctuation at first when they pass through the second sampling volume. As a result an amplitude of an output signal at the second peak detector 20 changes and then with some delay equal to time of an acoustic diffuser pass from the second sampling volume to the first sampling volume $\tau$, an amplitude of an output signal at the first detector 14 also changes. Statistical data accumulation of output signals of peak detectors provides a formation of a CCF maximum, its coordinate along a time axis is equal to $\tau$. So a local gas velocity is determined by the expression:

$$w_g=l/\tau,$$

where l is the distance between the first and the second sampling volumes.

Figure 4:
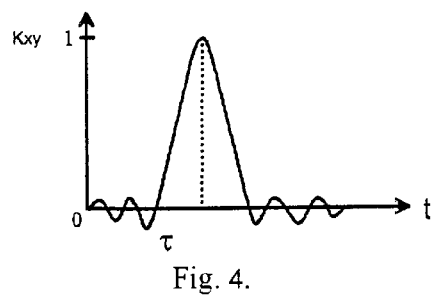
FIG. 4 typical form of a cross-correlation function for output signals of peak detectors.

A typical form of the cross-correlation function is shown in FIG. 4.

Figure 5:
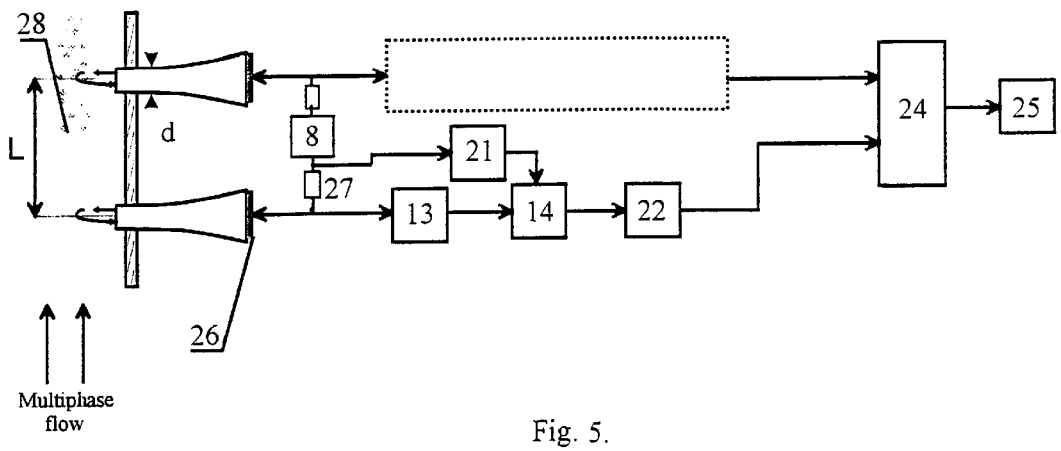
FIG. 5 block diagram of the local gas phase velocity meter for the variant of transducers located in series ("emission-reception" mode)

Another variant of acoustic sensing multiphase mixture by measuring of a local gas velocity is also possible. In this case two located in series acoustic transducers which operate in the mode "emission-reception" are used. The illustration of such a decision is presented in FIG. 5.

In this variant the velocity meter consists of two identical electro-acoustic channels, each one contains the following connected in series elements: an acoustic sensor 26, an amplifier 13, a peak detector 14 being strobed, an analogue-to-digital converter (ADC) 22 and also an electric pulse generator 8 connected to the sensor 26 through a sampling volume resistor 27 and a former of delayed strobe pulses 21. The former 21 is connected to a strobe input of the peak detector 14. Outputs of the channels are connected to a calculator 24 and then a display 25. Acoustic sensors are located inside a pipeline so that a flow 28 successively passes at first through a sampling volume of the first channel and then through a sampling volume of the second channel.

Figure 6:
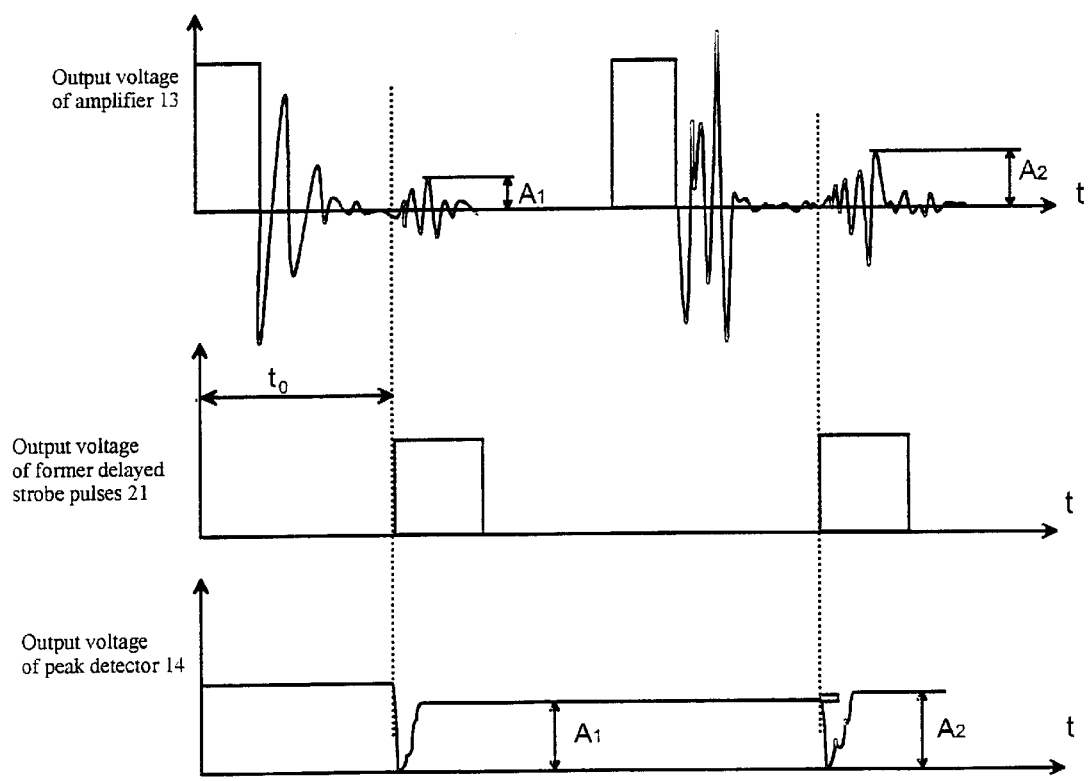
FIG. 6 voltage diagram of the signal processed in the block diagram presented in FIG. 5.

The meter operates in the following way. Electric pulses from the generator 8 are transmitted to the acoustic sensor 26 where they are transformed into ultrasonic signals and emitted into the flow 28. Then a part of acoustic energy reflects from medium diffusers and comes back to the sensor 26, is amplified by the amplifier 13 and transmitted to the peak detector 14 being strobed. Simultaneously the delayed strobe pulse from the former 21 is transmitted to the strobe input of the peak detector 14 (see voltage diagram in FIG. 6). The resistor 27 executes uncoupling of an output of the generator 8 and an input of the amplifier 13. At the output of the peak detector 14 the voltage level proportional to an amplitude a of received signal is formed. Time of the strobe pulse delay relative to the pulse of the generator 8 to (see FIG. 6) is set taking into account passage time of the ultrasonic signal from the sensor to the sampling volume and back.

A signal amplitude at the output of the peak detector fluctuates according to emergence of acoustic diffusers in a sampling volume. Since the diffusers at first pass through the sampling volume of the first sensor and then through the sampling volume of the second sensor the maximum on their CCF is formed. Coordinate $\tau$ of this maximum along the time axis is determined by passage time of the diffusers from the first sensor to the second one. A velocity of the diffusers contained in a medium is determined by the following formula:

$$w_g = l/\tau,$$

where l is the distance between the first and the second sensors.

For calculation the CCF signals from the outputs of the peak detectors of the first and the second channels come through the ADC to the calculator 24. Results of calculations are shown on the display 25.

Figure 7:
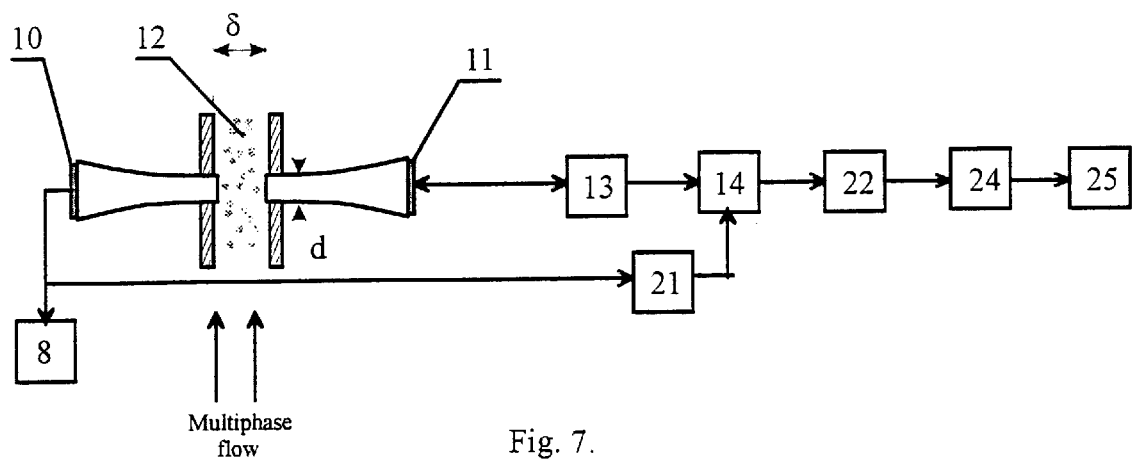
FIG. 7 block diagram of the local gas phase velocity meter while working of a pair of transducers in the mode of autocorrelation function forming.

Besides the above-described variant the local gas velocity meter can be implemented using one transducer with a pair of emitter and receiver of acoustic signals and also located inside the pipeline. The emitter and receiver are placed opposite to each other and form a sampling volume. The distance between them is chosen so that a mixture freely flows through the sampling volume. By an acoustic diffuser passage through a gap an ultrasonic signal is damped for a time equal to the time of the diffuser passage through the sampling volume. On the basis of these events an autocorrelation function of output signals is formed and the time of the diffuser passage through the sampling volume is determined. Illustration of this variant of the local gas velocity meter is shown in FIG. 7. In this case the circuit contains elements connected in series: electric pulses generator 8, emitter 10 acoustically connected with receiver 11, amplifier 13, peak detector 14 being strobed, analogue-to-digital converter (ADC) 22, calculator 24 and display 25. The generator 8 is also connected through a former of delayed strobe pulses 21 with a strobe input of the peak detector. The space between the emitter (10) and receiver (11) represents a sampling volume 12.

Figure 8:
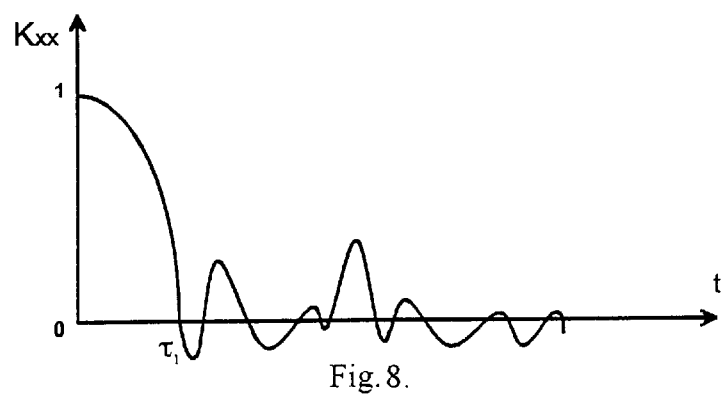
FIG. 8 typical form of an autocorrelation function for output signals of peak detectors.

The velocity meter operates in the following way. Electric pulses from the generator 8 come to the emitter 10, are transformed into ultrasonic signals and through the sampling volume 12 come to the receiver 11, then to the amplifier 13 and to the peak detector 14. Simultaneously strobe pulses from the former 21 delayed for the time of the signal propagation from the emitter to the receiver are sent to the strobe input of the peak detector. Voltage from the input of the peak detector 14 proportional to the amplitude of a received signal is transferred to the ADC 22, then to the calculator 24 and the display 25. When diffusers of acoustic signal with sizes of particles less than the sampling volume are present in the flow every diffuser penetrating into the sampling volume will induce amplitude fluctuation of received signal. To the first approximation the time of amplitude fluctuation is equal to the time of diffuser passage through the sampling volume. Autocorrelation function determines the average time for statistical sampling of data. A typical form of the autocorrelation function is shown in FIG. 8. So the local gas velocity can be calculated by the formula:

$$w_g = d/\tau_1,$$

where d is a linear size of a piezotransmitter plate in the flow direction, $\tau_1$ is a main lobe width of the autocorrelation function (FIG. 8).

Figure 9:
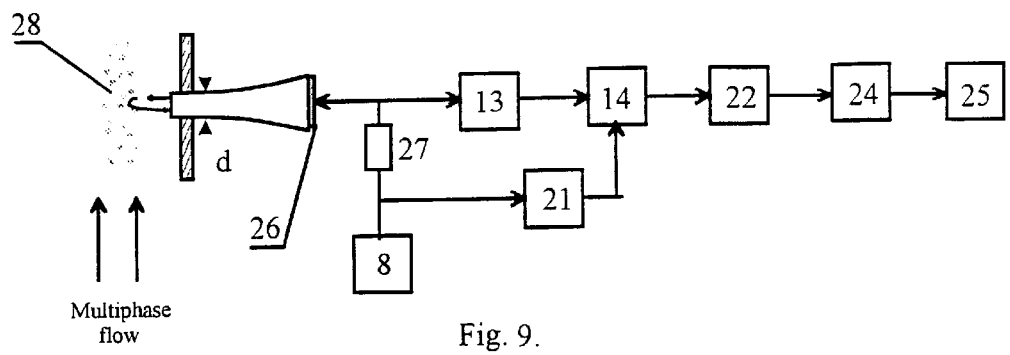
FIG. 9 block diagram of the local gas phase velocity meter while working of one transducer in the "emission-reception" mode.

One more variant of the local gas velocity meter is also possible. Its technical realization is shown in the FIG. 9. In this variant a circuit of the velocity meter includes the following elements connected in series: an acoustic transducer 26, an amplifier 13, a peak detector 14 being strobed, an analog-to-digital transmitter 22, a calculator 24 and a display 25 and also a generator 8 connected through a resistor 27 with the transducer 26 and connected through a former of delayed strobe pulses 21 with a strobe input of the peak detector 14. The transducer 26 is situated inside a pipeline so that multiphase flow 28 crosses an acoustic field of the transducer 26 perpendicularly to the flow direction.

Figure 10:
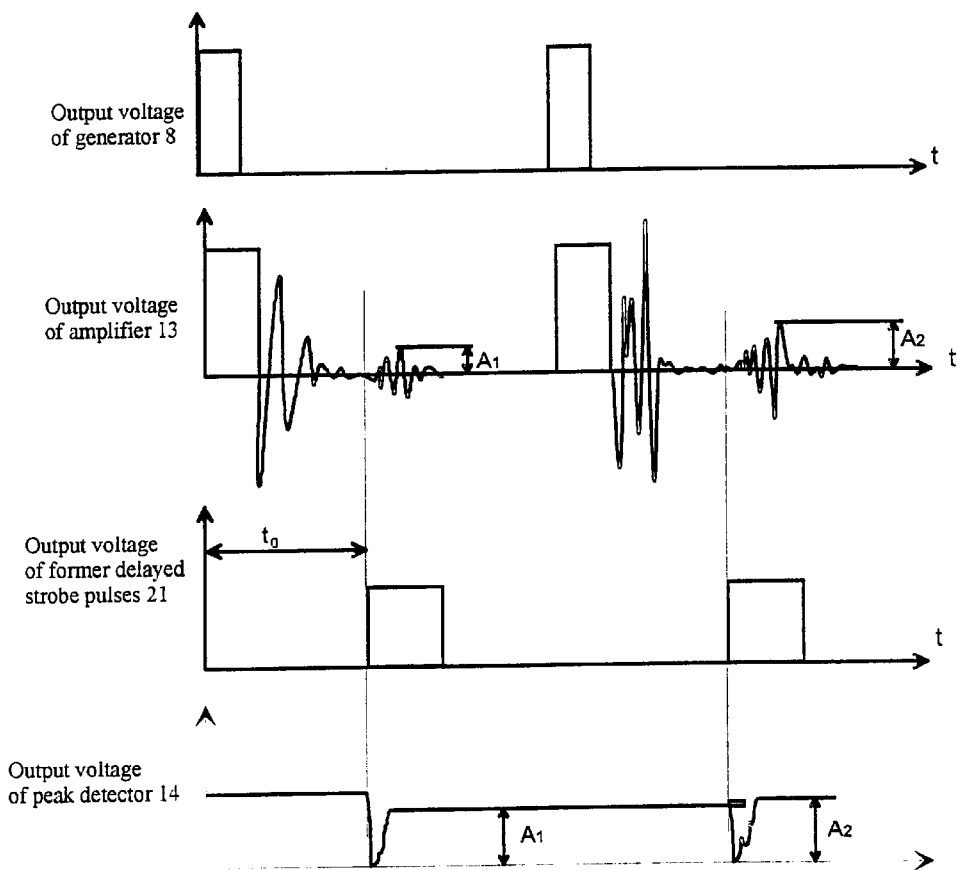
FIG. 10 voltage diagram of the signal processed in the block diagram presented in the FIG. 9.

The meter operates in the following way. Voltage pulses from the generator 8 are transmitted through the resistor 27 to the transducer 26 where they are transformed into acoustic signals and emitted into the flow 28 perpendicularly to its direction. A portion of acoustic energy is reflected from acoustic diffusers of the multiphase medium (the main part of them are gas inclusions) and returns to the transducer 26 where it is transformed into electric signals which through the amplifier 13 come to the peak detector 14. Simultaneously a delayed strobe pulse from the former 21 is transmitted to the strobe input of the peak detector 14 (see the voltage diagram shown in FIG. 10).

A resistor uncouples the output of the generator 8 and the input of the amplifier 13. The voltage amplitude at the output of the peak detector 14 is proportional to an amplitude of the received signal.

The time of delay of a strobe pulse to (see FIG. 10) relative to a generator 8 pulse is set according to the time of ultrasonic signal passage from the transducer 26 to the sampling volume and back.

Figure 11:
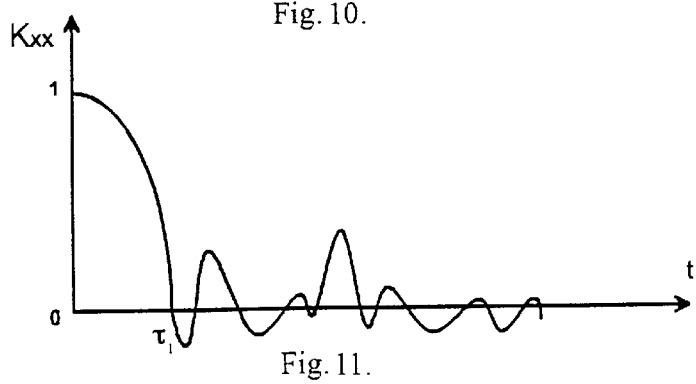
FIG. 11 autocorrelation function form of the of the output signal of the peak detector in the variant of using one transducer.

A signal amplitude at the output of the peak detector fluctuates according to emergence of acoustic diffusers in the sampling volume. To the first approximation the time of fluctuation is equal to the time of diffuser pass through the sampling volume. Under condition that the sizes of diffusers are much smaller than the size of the sampling volume the local gas velocity can be determine by autocorrelation of the signals by the formula:

$$w_g = d/\tau_1,$$

where d is a linear size of a piezotransmitter plate in the flow direction, $\tau_1$ is a main lobe width of the autocorrelation function (FIG. 11).

Figure 12:
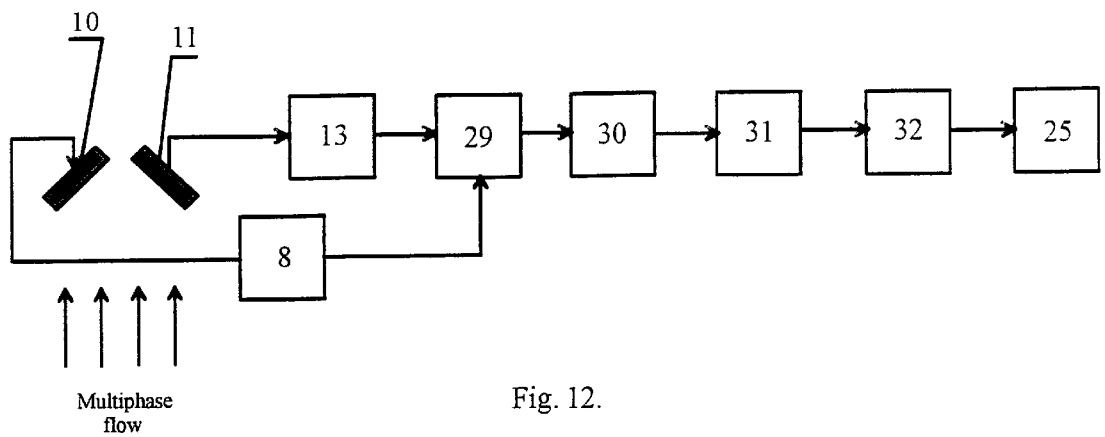
FIG. 12 block diagram of the ultrasonic Doppler's meter of the gas phase local velocity.
Figure 13:
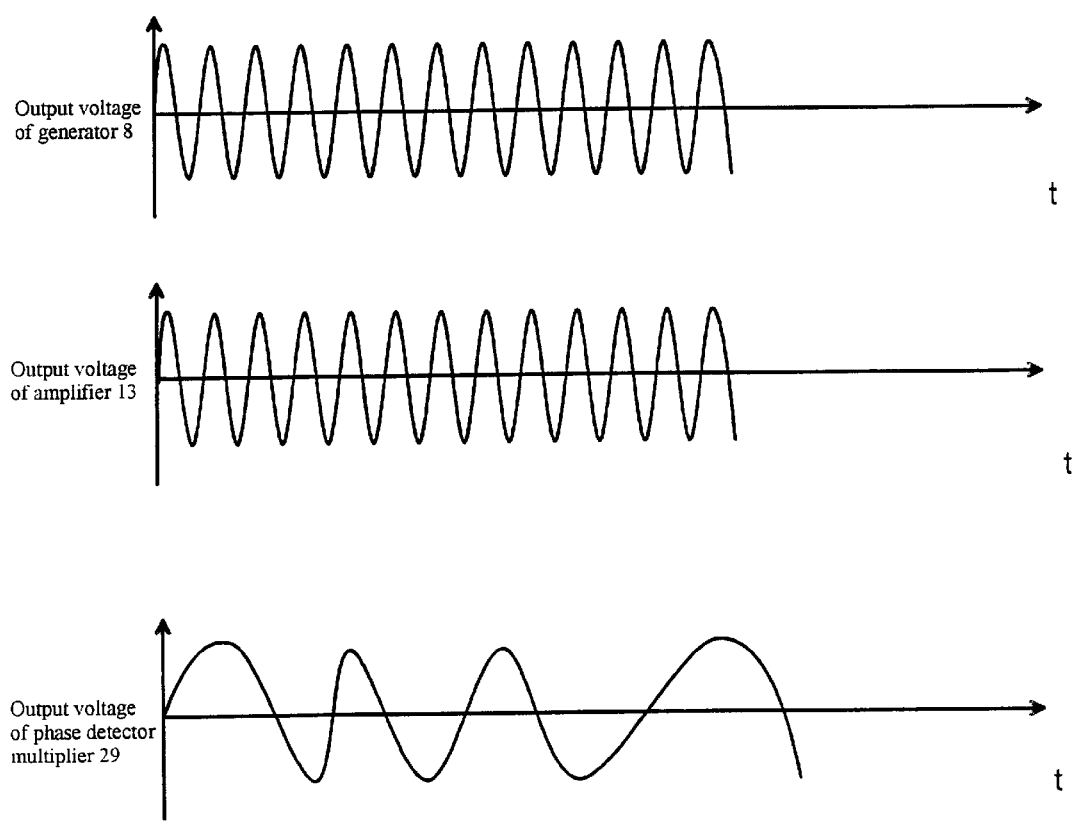
FIG. 13 typical form of signals in the block diagram of ultrasonic Doppler's meter of velocity presented in the FIG. 12.

Besides the above described variants another implementation of the ultrasonic local gas velocity meter using Doppler's method of velocity determination is also possible. In this case the emitter and receiver with linear sizes up to 3 mm are set inside calibrated pipeline divisions under a fixed angle relative to each other. The circuit of the meter is shown in FIG. 12. The meter contains an electric pulses generator 8 connected to emitter 10. Receiver 11 is connected through an amplifier 13 to a phase detector-multiplier 29. The following elements are connected in series to the output of the detector 29: a low-pass filter 30, the second amplifier 31, a signal spectrum calculator 32 and a display 25. A signal is processed in the measurement circuit in the following way. After the reflection of emitted ultrasonic oscillations from acoustic diffusers of a flow the acoustic signals come to the receiver 11, are transformed into voltage signals, are transmitted through the amplifier 13 to a first input of the phase detector 29. A voltage signal from the generator 8 is sent to a second input of the detector 29. From an output of the detector 29 low frequency signals are sent through a filter 30 and an amplifier 31 to the calculator 32 where a Doppler's frequency proportional to a velocity of acoustic diffusers approach to a transducer is determined and then a local gas velocity is calculated. Results of processing are sent to the display 9. Signal processing in the circuit is shown in FIG. 13.

Figure 14:
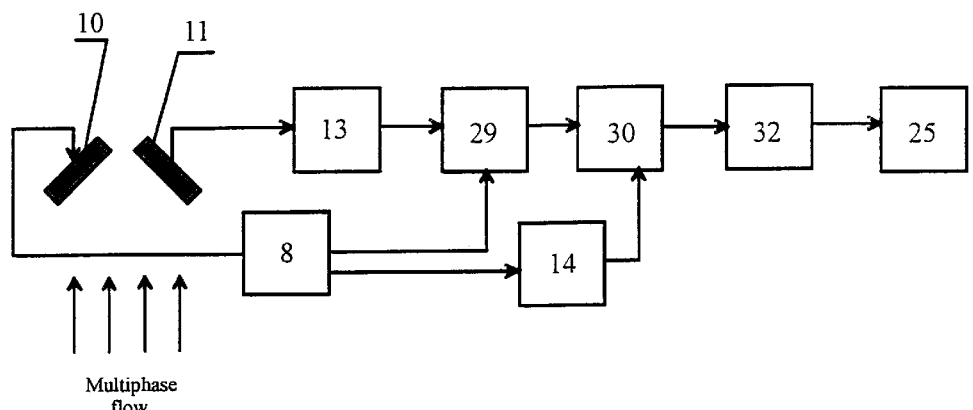
FIG. 14 second variant of the block diagram of the ultrasonic Doppler's meter for measuring of the gas phase local velocity.

Another variant of technical implementation of the ultrasonic Doppler's local gas velocity meter is demonstrated in FIG. 14. Emitter and receiver with linear sizes up to 3 mm are also disposed inside calibrated pipeline divisions at a fixed angle relative to each other. Measuring circuit of the meter contains a voltage pulses generator 8 connected to an emitter 10. A receiver 11 is joined through an amplifier 13 to a phase detector-multiplier 29, its output is connected to a "sampling-storage" block 30. The second input of the phase detector 29 is linked to the generator 8. An input of the "sampling-storage" block 30 is connected to generator 8 through the former of delayed strobe pulses 21. An output of the block 30 is connected to the calculator 32 and then the display 25.

Figure 15:
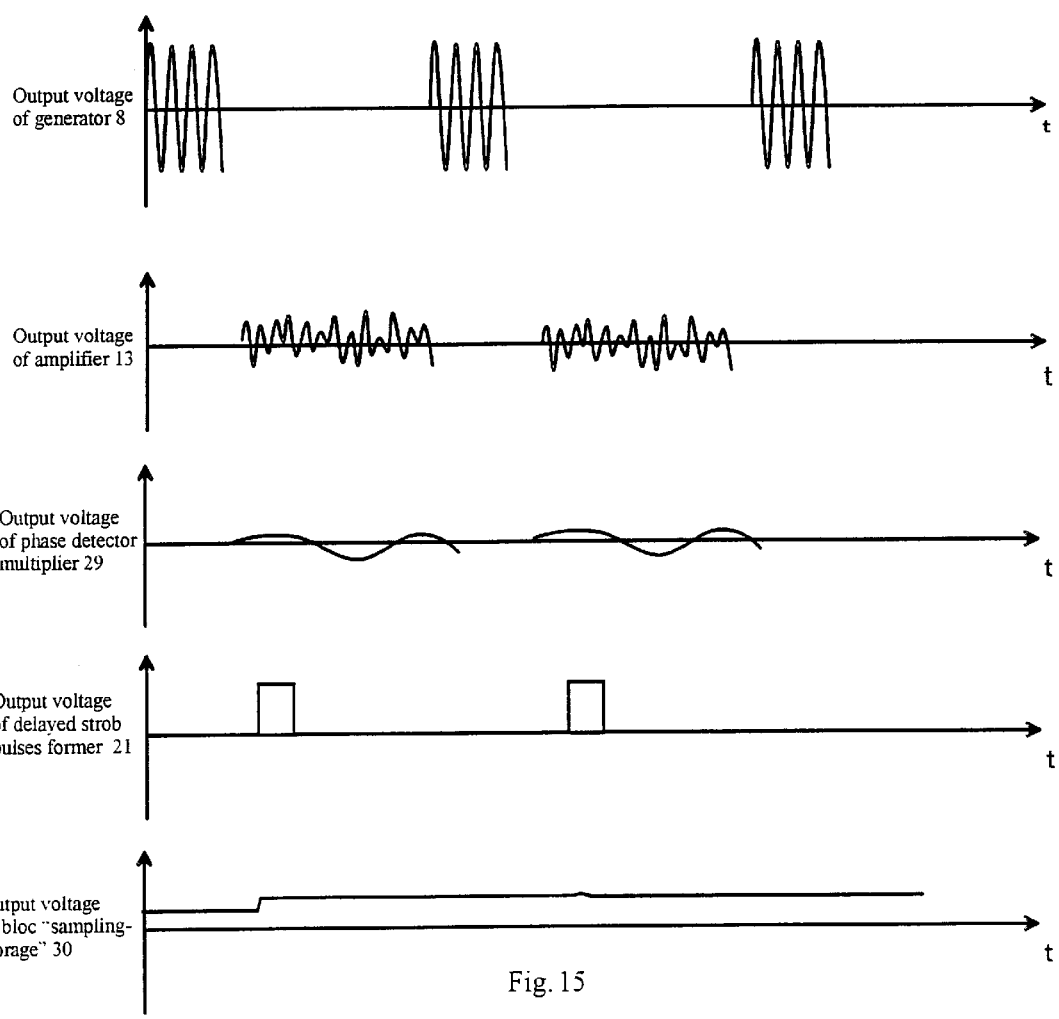
FIG. 15 voltage diagram of a signal processed in the block diagram presented in FIG. 14.

The meter operates in the following way. Voltage pulses from the generator 8 are transmitted to the emitter 10 and induce acoustic pulses propagating opposite flow direction. Pulses reflected from acoustic diffusers mainly from gas bubbles come to the receiver 11 and through the amplifier 13 are transmitted to the first input of the phase detector-multiplier 29. A high-frequency signal from the generator 8 is sent to the second input of the detector 29. A low-frequency signal from the detector 29 is sent to the "sampling-storage" block 30 which registers the signal at its input at the moments of time determined by the time position of the delayed strobe pulse from the former 21. Spectral processing of the signal from the "sampling-storage" block 30 is executed in the calculator 32 where the Doppler's frequency proportional to the approach velocity of acoustic diffusers to the transmitter is isolated and a local gas velocity is calculated. Results of processing are shown on the display 25. Signal processing in the circuit is shown in FIG. 15.

Figure 16:
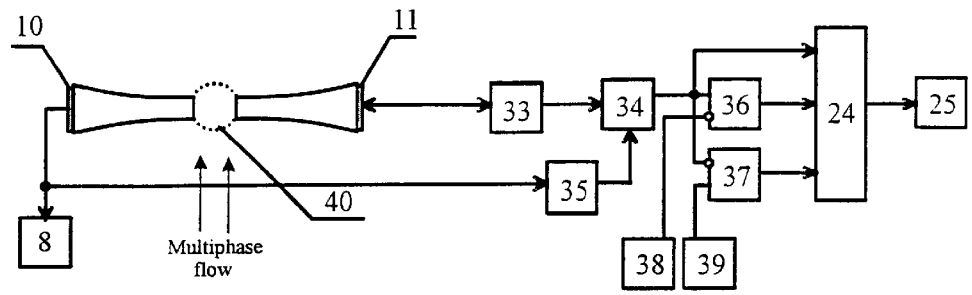
FIG. 16 block diagram of the gas content meter in a multiphase mixture is presented.

Ultrasonic gas content meter (see FIG. 16) contains a voltage pulses generator 8 connected in series to an emitter 10, which is acoustically linked to a receiver 11, an amplifier 33 and a peak detector 34 being strobed. The generator 8 is also connected to a strobe input of the peak detector 34 through a former of delayed strobe pulses 35. Output of the peak detector is linked to a direct input of a first comparator 36, to an inverse input of a second comparator 37 and to a calculator 24. Outputs of comparators 36 and 37 are also connected to the calculator 24 and then to a display 25. An inverse input of the first peak detector and a direct input of the second peak detector are connected to a first voltage setting device 38 and a second voltage setting device 39 respectively. The emitter and the receiver 10 and 11 are fixed one against the other forming a sampling volume 40.

Figure 17:
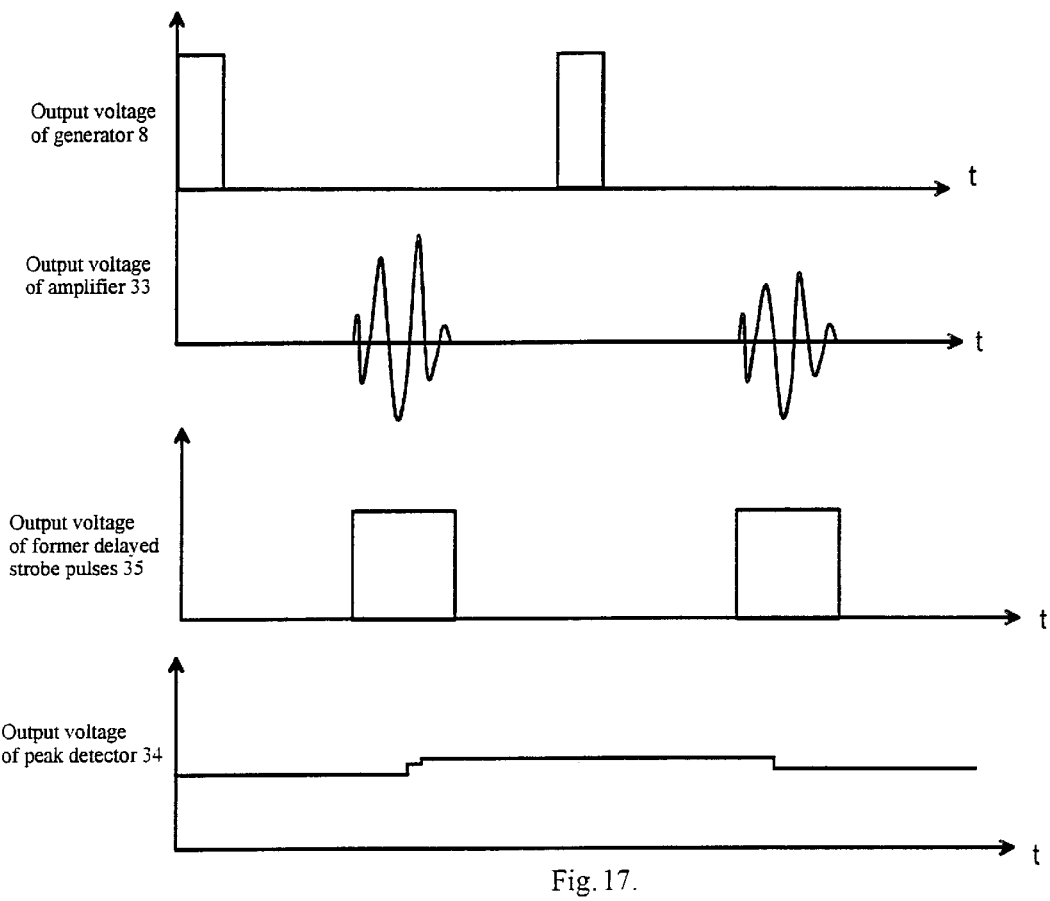
FIG. 17 diagram of a signal processed in the block diagram of the gas content meter.

The meter operates in the following way. Rectangular voltage pulses produced by the generator 8 are transformed by the emitter 10 into ultrasonic pulses which are emitted into the sampling volume 40, reach the receiver 11, are transformed into voltage pulses and transmitted trough the amplifier 33 to the peak detector 34. A diagram of the signal processing in the elements of a meter measuring circuit is presented in the FIG. 17. At the output of the peak detector 34 a level proportional to the amplitude of a signal being received at the moment of coming of a delayed strobe pulse is formed.

Figure 18:
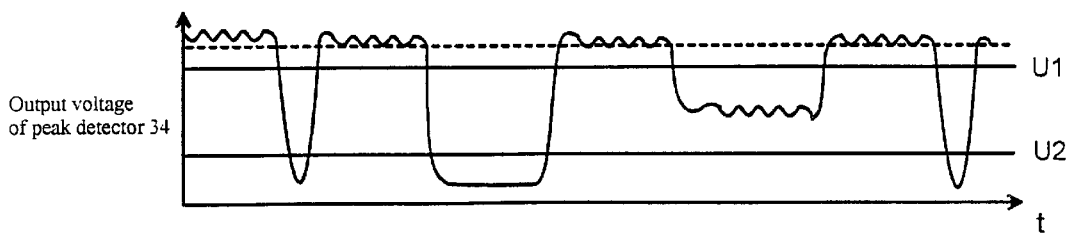
FIG. 18 diagram of an output signal of the peak detector.

The amplitude of the signal being received is determined by the gas volume concentration in the sampling volume 40. When the sampling volume is filled with liquid without gas inclusions the amplitude of the signal being received is at maximum and the voltage level at the input of peak detector 34 is higher than the voltage of the setting device 38 (U1). That induces actuation of the comparator 36 and forming of an individual logic signal at its output. The logic signal is sent to the calculator 24 and is considered by the calculator 24 as a situation with gas volume concentration $\phi=0$ (see FIG. 18). Sizes of gas inclusions in a real multiphase flow are different and can be both less and greater than a size of the sampling volume 40. When the sizes of bubbles or gas plugs exceed the size of the sampling volume the propagation of the ultrasonic pulses is totally blocked, the amplitude of the signal being received diminishes to a minimum determined by a level of noises, and a voltage level at the output of the peak detector 34 is also minimum and is below a voltage of the setting device 39 (U2). In this case the comparator 37 actuates and produces an individual logic signal considered by the calculator 24 as a situation with a gas volume concentration $\phi=1$.

When the sizes of the gas bubbles are smaller than the size of the sampling volume 40 an output signal amplitude of the of peak detector 34 ranges from U1 to U2 (see FIG. 18) and is described by the following relationship:

$$U = U^{max} exp(-k \cdot n_b \cdot d_b^2), \tag{20}$$

where $U^{max}$ is an amplitude of the signal when the liquid phase fills the controlled volume, k is a proportionality factor determined by geometric sizes of the sensor, by the ultrasonic frequency and so on, $n_b$ is concentration of gas bubbles, $d_b$ is diameter of gas bubbles.

Taking into account that the concentration of bubbles changes continuously in the sampling volume owing to the mixture flowing the signal amplitude also fluctuates. Number of bubbles in the sampling volume is determined by Puasson's law. So through the measurement of an average value of the received signal and of its dispersion values $n_b$ and $d_b$ are calculated using a known mathematical model by the calculator 24. The volume gas content is determined according to the formula:

$$\varphi_3 = N \cdot \frac{\pi d^3}{6} \cdot \frac{1}{V}, \tag{21}$$

where V is the sampling volume, $N = n_b \cdot V$ is a number of the bubbles in the sampling volume.

The gas phase concentration in case of variable composition of the gas inclusions in the flow is determined by the relationship:

$$\varphi = \frac{t_2 \cdot 1 + t_3 \cdot \varphi_3}{T}, \tag{22}$$

$T = t_1 + t_2 + t_3$ is time of averaging, where $t_1$ is a period of time when the gas inclusions are absent in the sampling volume, $t_2$ is a period of time when the gas inclusions presented by the bubbles of big diameter and also the gas plugs are present in the sampling volume, $t_3$ is a period of time when small bubbles are present in the sampling volume.

The size of the sampling volume is chosen according to conditions of either technical implementation or application of the sensor, as a rule the size is smaller than 1 mm$^3$.

Figure 19:
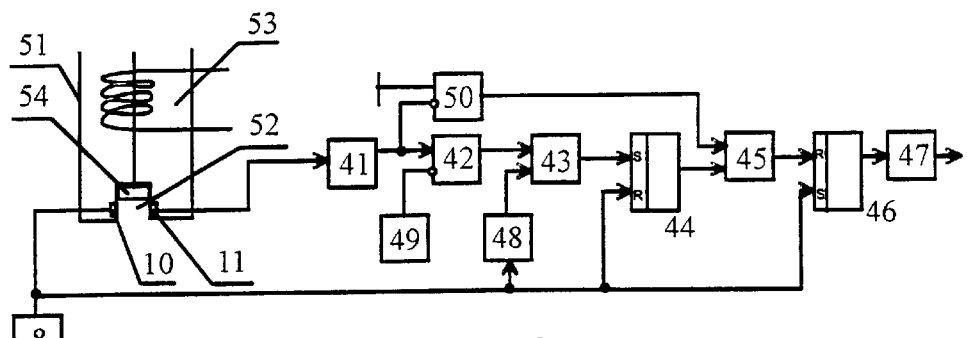
FIG. 19 block diagram of the ultrasonic meter of volume concentrations of liquid components.

Block diagram of the ultrasonic meter of volume concentrations of liquid components is shown in the FIG. 19. A measuring circuit of the meter comprises a generator of voltage pulses 8 and the following elements connected to it in series: an emitter 10 acoustically linked to a receiver 11, an amplifier 41, a first comparator 42, a first element 2& 43, a first RS-trigger 44, a second element 2& 45, a second RS-trigger 46 and a "duration-amplitude" converter 47. The generator 8 is also connected to a former of delayed strobe pulses 48 and to the second inputs of the RS-triggers 44 and 46. The second input of the first comparator 42 is linked to a voltage setting device 49. An output of the amplifier 41 is connected to a second comparator 50, its output is linked to the second input of the second element 2& 45. An output of the former of delayed strobe pulses 48 is connected to the second input of the first element 2& 43.

The emitter and receiver are mounted in a tool body 51 one opposite the other thus forming a sampling volume 52.

The tool body 51 is equipped by a heater 53 and an element 54 for mechanical cleaning of the sampling volume 52.

The ultrasonic meter of volume concentration operates in the following way.

Rectangular voltage pulses produced by the generator 8 are transformed into ultrasonic pulses by the emitter 10. After passing through the sampling volume 52 they reach the receiver 11 and are transformed into electric pulses. Then the signal through the amplifier 41 comes to the direct input of the first comparator 42.

Simultaneously with sending the voltage pulse the first RS-trigger 44 is switched into a state "zero" and the second RS-trigger 46—into a state "one".

Since an inverse input of the comparator 42 is connected to the voltage setting device 49, actuation of the comparator 42 occurs when the amplitude of the received signal excesses a set voltage. Pulses from an output of the comparator 42 are transmitted to an S-input of the first RS-trigger 44 through the first element 2& 43 being strobed by pulses from the output of the former of delayed strobe pulses 48 and switch it into the state "one" (see the diagram of voltages in FIG. 20). A time lag is determined the by time of the ultrasonic pulses propagation from the emitter 10 to the receiver 11. Using a delay element excludes false actuations of the meter stipulated by electric and acoustic noises.

Figure 20:
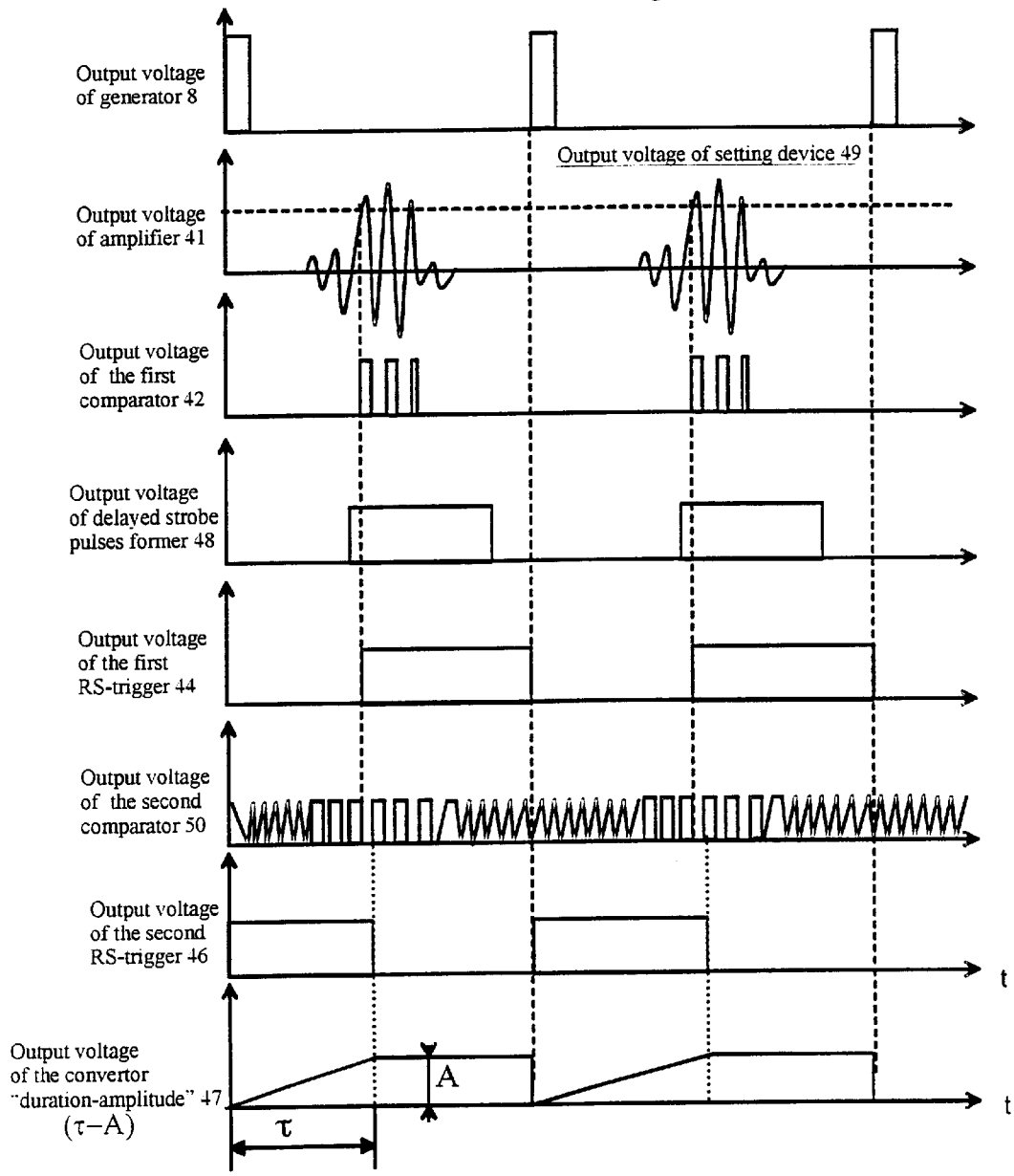
FIG. 20 voltage diagram of a signal processed in the block diagram for measuring liquid phase volume concentrations.

Since one of the inputs of the second comparator 50 is connected to the ground wire it produces voltage pulses every time when the amplitude of the received signal crosses a "zero" mark so fixing even a weak signal (see FIG. 20). An output signal of the comparator doesn't depend on the amplitude of the received signal.

A signal from an output of the first RS-trigger 44 transmitting to one of the inputs of the second element 2& 45 permits a passage through it of the signal from the second comparator 50 which indicate that the received signal crossed a "zero" mark. The first "zero" mark crossing induces actuation of the second RS-trigger 46 thus switching it into "zero" state. The voltage pulses formed so have durations proportional to passage time of the ultrasonic pulses from the emitter 10 to the receiver 11 and don't depend on ultrasonic pulses amplitudes. Then these pulses are transformed in the converter 47 into an amplitude signal proportional to their durations which is transmitted to the calculator and the monitor.

Figure 21:
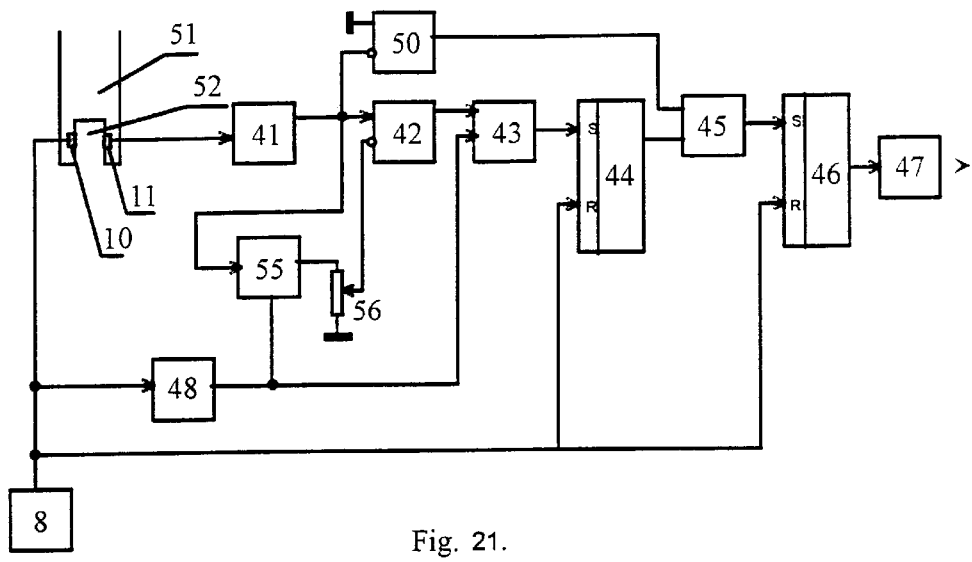
FIG. 21 second variant of the block diagram of the ultrasonic meter of volume concentrations of liquid components.

In the second variant of the ultrasonic meter of volume concentrations of liquid components (see FIG. 21) a voltage setting device is implemented as a peak detector 55 being strobed (see FIG. 21). Its input is connected to the output of the amplifier 41, a strobe input is linked to the output of the former of the delayed strobe pulses 48 and an output of the peak detector 55 is connected to the second input of the first comparator 42 through a voltage divider 56.

Figure 22:
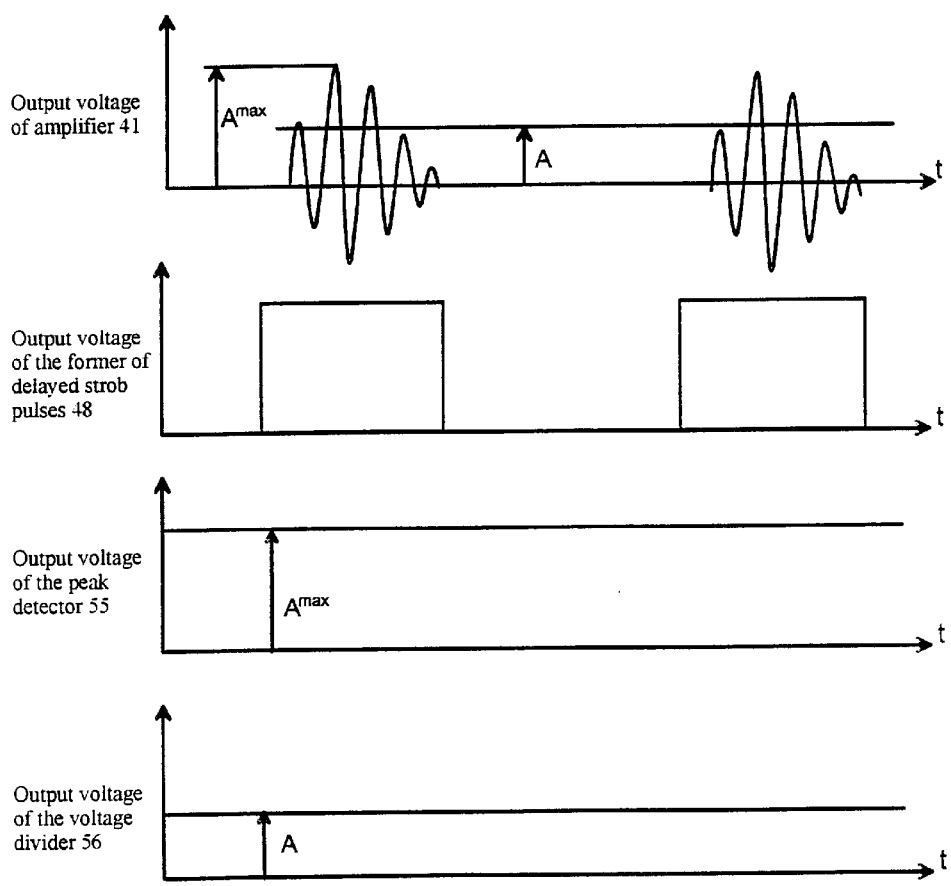
FIG. 22 voltage diagram of a signal for the second variant of the block diagram of the volume concentration meter of liquid components.

The voltage setting device operates in the following way. A voltage signal from the amplifier 41 is transmitted to the peak detector 55. Simultaneously with a time lag determined by the passage time of the ultrasonic pulses from the emitter 10 to the receiver 11 the signal from the former of the delayed strobe pulses 48 comes to its strobe input (see FIG. 22). As a result a voltage potential equal to a maximum value of the signal amplitude is formed at the output of the peak detector 55. The voltage signal passed through the divider 56 is damped so that secure actuation of the first comparator 42 is guaranteed at the selected half-wave of the signal by its variations due to changes of the controlled medium properties and temperature and owing to aging of measuring circuit elements an so on.

The use of such voltage setting device permits to support automatically the level of the comparator actuation by significant (10-fold) changes of signal attenuation in the medium stipulated, for example, by emergence of gas bubbles within the sampling volume, by change of dispersion of components and by other reasons.

The operation of the meters of local values $w_{g,1}$, $w_{g,2}$, $\phi_1$, $\phi_2$ and $W$ is controlled according to a set program by processor. Time averaging and cross-section averaging of the calibrated pipeline divisions of the above indicated values are also executed by means of the processor. The volume flow rates of the multiphase flow components such as liquid, oil, water and gas $Q_l$, $Q_{oil}$, $Q_w$, $Q_g$ are moreover determined according to the formulas (16, 18, 19) by the processor.

Though the invention described in particular for use with an oil, water and gas mixture, it must be understood that the principle of the invention, as set forth in the appended claims, is applicable for other mixtures also.

Further, though the example of FIG. 1 shows an order of pipeline divisions with decreasing cross-section areas seen in the flow direction an opposite order of pipeline line divisions, that is with increasing cross-section areas seen in the flow direction, can be used.

What is claimed is:

1. Method for determining flow rates of gas and liquid phases of a flow of a multiphase mixture along a pipeline, comprising the steps of:
   a. measuring a real velocity w of at least one phase of the mixture in a section of the pipeline;
   b. measuring an acoustic conductivity of the mixture in the pipeline section;
   c. determining a volume concentration φ of a gas phase of the mixture in the pipeline section on the basis of the measured acoustic conductivity of the mixture in the pipeline section;
   d. determining volume flow rates of the gas phase Qg, and of first and second components Q1, Q2 of the liquid phase $Q_l$ of the mixture by using values of said real velocity w and said volume concentration;
further comprising, with said pipeline section being a first pipeline section:
   e. providing a second pipeline section in series with the first pipeline section, the first and second pipeline sections having different cross sections, such that a change in flow velocity of the mixture occurs at the junction of the two sections;
   f. measuring the real velocity in the second pipeline section;

g. measuring the acoustic conductivity in the second pipeline section;

h. determining the volume concentration ø of the gas phase in the second pipeline section on the basis of the measured acoustic conductivity of the mixture in the second pipeline section;

i. determining a volume concentration W of different liquid phase components of the mixture on the basis of the measured acoustic conductivity of the mixture in at least one pipeline section;

j. determining the volume flow rates Qg, $Q_l$, Q1, Q2 by using values of the real velocity w and the volume concentrations obtained for the first and second pipeline sections in combination.

2. Method according to claim 1, wherein the area $F_1$ of the cross-section of the first pipeline section differs from the area $F_2$ of the cross-section of pipeline section $F_2=kF_1$, where k≠1.

3. Method according to claim 1, wherein the area $F_1$ of the cross-section of the first pipeline section differs from the area $F_2$ of the cross-section of pipeline section $F_2=kF_1$, where k≠1, and the volume flow rate value of liquid phase is determined by the formula:

$$Q_l = k/(k-1)F_1[w_2(1-\phi_2)-w_1(1-\phi_1)],$$

where
$w_1, w_2$ is an average real velocity of gas phase in the first pipeline section and the second pipeline section respectively,
$\phi_1, \phi_2$ is an average real volume gas concentration in the mixture in the first pipeline section and the second pipeline section respectively;
the volume flow rate of gas phase is determined by:

$$Q_g=F_1 w_1 \phi_1 \text{ or } Q_g=F_2 w_2 \phi_2,$$

the volume flow rate of the first component of liquid phase is determined by:

$$Q_1=WQ_l,$$

and the volume flow rate of the second component of liquid phase is determined by:

$$Q_2=(1-W)Q_l.$$

4. Method according to claim 1, wherein the velocity w of gas phase is measured at different radial locations in each of said cross-sections of the first and second pipeline sections, and measured local velocity values for each cross-section are averaged to provide a value for use as velocity value in calculations.

5. Method according to claim 1, wherein the concentration of gas phase φ is measured at different radial locations in each of said cross-sections of the first and the second pipeline sections, and measured volume concentration values for each cross-section are averaged to provide a value for use as concentration value in calculations.

6. Method according to claim 1, wherein measurements are carried out by the use of ultrasonic transducers.

7. Method according to claim 1, wherein volume concentrations of liquid phase components W of the mixture are determined by using ultrasonic transducers in at least one cross-section in at least one of the pipeline sections and by measuring time of passage of ultrasonic pulses through the mixture from the transducers.

8. Method according to claim 1, wherein volume concentrations of gas phase components φ of the mixture are determined by using ultrasonic transducers in at least one cross-section of the first and the second pipeline sections and by measuring amplitude of ultrasonic pulses passed through the mixture from the transducers.

9. Method according to claim 1, wherein velocities w of the mixture phases are determined by using ultrasonic transducers in at least one cross-section of the first and the second pipeline sections and by cross-correlation or auto-correlation methods.

10. Method according to claim 1, wherein velocities w of the mixture phases are determined by using ultrasonic transducers in at least one cross-section of the first and the second pipeline sections and by measuring Doppler frequency of ultrasonic pulses from the transducers.

11. Method according to claim 1, wherein measurements are carried out by the use of electrical conductivity transducers.

12. Met hod according to claim 1, wherein measurements are carried out by the use of electrical capacity transducers.

13. Method according to claim 1, wherein measurements are carried out by the use of optical sensors.

14. Method according to claim 1, wherein volume concentrations of gas phase components φ of the mixture are determined by using ultrasonic transducers in at least one cross-section of the first and the second pipeline sections and by measuring amplitude of ultrasonic pulses passed through the mixture from the transducers, and the liquid phase components of the mixture are water and oil.

15. Device for determining flow rates of gas and liquid phases of a flow of a multiphase mixture along a pipeline, comprising:

a. a velocity sensor which is arranged in a section of the pipeline and which is connected to circuitry for measuring a real velocity w of at least one phase of the mixture in the pipeline section;

b. an acoustic conductivity sensor which is arranged in the pipeline section and which is connected to circuitry for measuring an acoustic conductivity of the mixture in the pipeline section and for determining a volume concentration φ of the gas phase of the mixture in the pipeline section on the basis of the measured acoustic conductivity of the mixture in the pipeline section;

c. a processor (p. 24 1. 34) which is connected to said circuitry for determining volume flow rates of the gas phase Qg, and of first and second components Q1, Q2 of the liquid phase $Q_l$ of the mixture by using values of said real velocity w and said volume concentration;

further comprising with said pipeline section being a first pipeline section:

d. a second pipeline section which is arranged in series with the first pipeline section, the first and second pipeline sections having different cross sections, such that a change in flow velocity of the mixture occurs at the junction of the two sections;

e. a further velocity sensor which is arranged in the second pipeline section and which is connected to circuitry for measuring a real velocity w of at least one phase of the mixture in the second pipeline section;

f. a further acoustic conductivity sensor which is arranged in the second pipeline section and which is connected to circuitry for measuring an acoustic conductivity of the mixture in the second pipeline section and for determining a volume concentration (p of the gas phase of the mixture in the second pipeline section on the basis of the measured acoustic conductivity of the mixture in the second pipeline section;

g. a liquid concentration sensor which is arranged in one of said pipeline sections and which is connected to further circuitry for determining a volume concentration W of different liquid phase components of the mixture on the basis of the measured acoustic conductivity of the mixture in said one pipeline section; and in which the processor is connected to the further circuitry and the processor uses values of the real velocity w and the volume concentrations obtained for the first and second pipeline sections in combination for determining the volume flow rates Qg, $Q_l$, Q1, Q2.

16. Device according to claim 15, wherein for each pipeline section the following means for measuring local flow characteristics of at least one phase of the mixture are used:

an ultrasonic gas velocity meter for measuring a real gas velocity w of the mixture based on correlation or Doppler's methods;

an ultrasonic volume gas concentration meter;

an ultrasonic meter of volume concentrations of liquid components.

17. Device according to claim 15, wherein meters with electrical capacity or electrical conductivity transducers for measuring local flow properties of at least one phase of the mixture are used.

18. Device according to claim 15, wherein for each pipeline section a gamma-meter for determining the volume gas concentration is used.

19. Device according to claim 15, wherein for each pipeline section disposed vertically an apparatus for determining the volume gas concentration by means of measuring a static pressure difference is used.

20. Device according to claim 15, wherein the gas velocity meter measures the velocity w of gas phase at different radial locations in each of said cross-sections of the first and the second pipeline sections, and measured local velocity values for each cross-section are averaged to provide a value for use as velocity value in calculations.

21. Device according to claim 15, wherein the volume gas concentration meter measures the concentration of gas phase ϕ at different radial locations in each of said cross-sections of the first and the second pipeline sections, and measured volume concentration values for each cross-section are averaged to provide a value for use as concentration value in calculations.

22. Device according to claim 15, wherein the area $F_1$ of the cross-section of the first pipeline section differs from the area $F_2$ of the cross-section of pipeline section by $F_2=kF_1$, where k≠1.

23. Device according to claim 15, further comprising a processor calculating the volume flow rate value of liquid phase by the formula:

$$Q_l=k/(k-1)F_1[w_2(1-\phi_2)-w_1(1-\phi_1)],$$

where $w_1$, $w_2$ is an average real velocity of gas phase in the first pipeline section and the second pipeline section respectively, $\phi_1$, $\phi_2$ is an average real volume gas concentration in the mixture in the first pipeline section and the second pipeline section respectively;

calculating the volume flow rate of gas phase by the formulas:

$$Q_g=F_1w_1\phi_1 \text{ or } Q_g=F_2w_2\phi_2,$$

calculating the volume flow rate of the first component of liquid phase by the formula:

$$Q_1=WQ_l,$$

and calculating the volume flow rate of the second component of liquid phase by the formula:

$$Q_2=(1-W)Q_l.$$

24. Device according to claim 15, wherein the sensed liquid phase components of the multiphase flow are water and oil.

* * * * *